United States Patent [19]

Gaisch et al.

[11] Patent Number: 4,709,710

[45] Date of Patent: Dec. 1, 1987

[54] PROCESS FOR IMPROVING TOBACCO

[75] Inventors: Helmut Gaisch, Cormondreche; Urs Nyffeler, Cortaillod, both of Switzerland

[73] Assignee: Fabriques De Tabac Reunies S.A., Neuchatel, Switzerland

[21] Appl. No.: 939,758

[22] Filed: Sep. 5, 1978

[51] Int. Cl.⁴ .................... A24B 15/20; A24B 15/24
[52] U.S. Cl. .................................. 131/308; 131/297
[58] Field of Search ............... 131/143, 142, 308, 356, 131/297; 210/601, 603, 605, 622, 903; 435/172, 262, 267

[56] References Cited

U.S. PATENT DOCUMENTS

| | | | |
|---|---|---|---|
| 2,317,792 | 4/1943 | Moser | 131/308 |
| 3,829,377 | 8/1974 | Hashimoato | 210/11 |
| 3,847,164 | 11/1974 | Mattina et al. | 131/143 |
| 4,039,438 | 8/1977 | Anderson | 210/11 |
| 4,043,936 | 8/1977 | Francis | 210/11 |
| 4,131,118 | 12/1978 | Gellatty et al. | 131/143 |
| 4,308,877 | 1/1982 | Mattina | 131/308 |
| 4,556,073 | 12/1985 | Gravely et al. | 131/297 |
| 4,557,280 | 12/1985 | Gravely | 131/308 |

FOREIGN PATENT DOCUMENTS 866445 8/1978 Belgium .

*Primary Examiner*—V. Millin
*Attorney, Agent, or Firm*—Arthur I. Palmer, Jr.; James F. Haley, Jr.; Margaret A. Pierri

[57] ABSTRACT

A culture of microorganisms requiring oxygen but capable of living anaerobically while using nitrates and/or nitrites as oxygen source, which are brought to their exponential growth phase under anaerobic conditions, and are made to react under like conditions on the nitrates and/or nitrites, until the nitrates and/or nitrites are reduced to the desired level and the effect of the microorganisms is then stopped.

9 Claims, No Drawings

PROCESS FOR IMPROVING TOBACCO

TECHNICAL FIELD

The invention concerns a process for treating tobacco whereby the nitrates and/or nitrites contained in tobacco are reduced.

Many tobaccos, Burley for example, contain salts of nitrates and/or nitrites. There are known fermentation processes in which these nitrogen salts are reduced by way of enzymes, however, only to a very small extent, and only as a side-effect of other enzymatic conversions.

BRIEF SUMMARY OF THE INVENTION

It is the purpose of this invention to reduce nitrates and/or nitrites to a lower level in tobacco in order to improve the smoking qualities thereof. The reduction of the nitrates and/or nitrites should take place as selectively as practicable without adversely affecting the other constituents in the tobacco.

The invention discloses the use of a culture of microorganisms that require oxygen but are capable of living anaerobically by denitration. The culture of microorganisms is brought to its exponential growth phase under anaerobic conditions in a nutrient solution adapted for the culture. The nutrient solution does not contain essential quantities of oxygen, i.e. less than 1 ppm., thereby causing the microorganisms to react under these substantially anaerobic conditions on the nitrates and/or nitrites until these are reduced to the desired level. After no longer than 24 hours, the effect of the microorganisms is stopped. Under these conditions, the microorganisms will remain in their exponential growth phase as long as the necessary oxygen requirements can be derived from the nitrates and/or nitrites.

DETAILED DESCRIPTION OF THE INVENTION

The microorganisms used herein utilize oxygen from the nitrates and/or nitrites, whereby the latter are degraded to the level of nitrogen or ammonia respectively. Nitrogen can escape to the atmosphere; and nitrogen compounds present in the form of ammonium salts, amino acids, and amines are similar to compounds normally found in tobacco.

Since the added culture is already in its exponential growth phase, the microorganisms have a lead of about 8 hours over other microorganisms present, which are still in their lag phase. Such microorganisms thus cannot catch-up this lead within the reaction period, which is maximally 24 hours, so that their effect is insignificant. This insures that the effect promoted by the invention will be selective.

Unfermented, air-dried tobaccos frequently have a nitrate content of about 50 g per kg dry weight. Nitrate quantities up to 80 g per kg dry weight have been found in extreme cases. The desired level of nitrates will depend on the ultimate use of the tobacco. For present purposes, however, the desired level of nitrates should be within the range of 3 to 20%, and preferably about 5% of the original content of the tobacco treated relative to the total weight of the anions of nitrate and/or nitrite.

It is possible to influence the selective effect of the invention further by allowing a highly concentrated culture of microorganisms to react so that the nitrates and/or nitrites are reduced to a minimal level within 12 to 24 hours, preferably within 20 hours; and thereafter the produced effect of the microorganisms is terminated immediately.

The minimal level, i.e., the level of nitrates and/or nitrites that can be achieved by the process of the invention without resorting to any extraordinary measures, depends on the quality of the tobacco, and amounts to from 0.01 to 0.1% of the original content of the treated tobacco, in each instance relative to the total weight of the anions of nitrates and/or nitrites.

With such a concentrated application of microorganisms, the desired level can be realized after a few hours so that the effect of the microorganisms can be terminated before the microorganisms of the culture have used up their approximately 8-hour lead or shortly thereafter.

The effect of the microorganism culture can be intensified by controlling the substantially anaerobic conditions for the microorganisms to an optimum with regard to temperature, humidity, pH level, nutrient supply, and by using a highly concentrated culture for reducing the nitrates and/or nitrites. The optimal conditions will be described hereinafter. The degree of reduction of nitrates and/or nitrites in tobacco may be ascertained analytically by known methods.

The effect of the microorganisms can be terminated by failure to maintain growing conditions for the microorganisms; for example, by greatly lowering or raising the temperature, by drying, and also by removing the microorganisms, as for example by filtration when the reaction is carried out in a liquid medium.

The microorganisms useful for this invention may be, for example, those selected from the genus Aerobacter, Pseudomonas, Micrococcus, or Echerichia; or, alternatively, they may be fungi such as from the genus Rhodutorula. Microorganisms belonging to the normal microflora of tobacco leaves are especially useful in that they have a particularly rapid denitrifying effect and do not adversely alter the tobacco in an undesireable way.

One aspect of the invention provides for using a culture of microorganisms obtained by inoculating a watery smear of nitrate-containing leaves or decayed leaves into a nutrient solution. The solution contains a source of oxygen required for growth, and is predominantly in the form of nitrates. The solution is buffered to between pH 6.6 and pH 7.5, and is then incubated anaerobically or substantially so at 25° to 35° C. for 15 to 25 hours with shaking. The thus prepared culture is then used as an active inoculum for the inoculation of another fresh nutrient solution, which is incubated in a similar manner. Transfers are repeated until a pure culture is obtained.

Preferably the smear is made from tobacco leaves. But a useable smear can also be obtained from forest soil comprising decayed leaves or containing decayed leaves therein. According to this method, a pure culture may be obtained wherein the microorganisms are in their active, i.e., their exponential growth phase. This culture is either used immediately or it is inactivated and preserved for later use.

The invention may advantageously be practiced utilizing a pure culture of *Enterobacter aerogenes*, preferably of type strain ATCC 13 048. Pure cultures of this type strain may be obtained from the American Type Culture Collection, 12301 Park Lawn Drive, Rockville, Md. 20852.

When, for example, the tobacco to be treated includes stems, denitration is greatly facilitated if the stems are first extracted with water to remove the soluble nitrates and/or nitrites. Thereafter, the aqueous extract is inoculated with the microorganism culture, the nutrient solution is added, and the mixture is incubated for 12 to 24 hours, and preferably 16 hours. Substantially anaerobic conditions favorable to the microorganisms are helpful. After an appropriate time period, the effect of the microorganisms is stopped by removing the active microorganisms by filtration, centrifugation, or the like. The treated extract solution from which the nitrates and/or nitrites have been removed is then reapplied to the original stems.

In yet another aspect of the invention when tobacco strips are treated, or leaves in which the nitrate and/or nitrite content of the mid-rib (stem) should only be moderately reduced, the process can be simplified by preparing an active suspension of the microorganism culture in the nutrient solution for inoculation. The tobacco is adjusted to a moisture content between 10 and 30%, and preferably 20%, and is then sprayed with the active suspension until a moisture content between 40 and 60%, and preferably 50%, is attained. The tobacco mixture is then incubated for 12 to 24 hours, and preferably 24. Substantially anaerobic conditions favorable to the microorganisms are maintained. After about 24 hours the reaction of the microorganisms is stopped by drying the tobacco to a moisture content between 10 to 30%, and preferably about 20%.

In some instances, as for example in making reconstituted tobacco, the tobacco materials are homogenized and made into a slurry. The slurry is cast into a sheet, which is then dried. In this instance, the microorganisms may be applied advantageously to the tobacco slurry. Preferably the tobacco is ground and mixed with water. The microorganism culture and the nutrient solution are added to the slurry, and the mixture is incubated for 12 to 24 hours, preferably 24 hours. Substantially anaerobic conditions favorable to the microorganisms are maintained. The effect of the microorganisms is stopped by casting the slurry into or onto sheets and drying them to a moisture content between 10 and 30%, preferably 15%.

The microorganism culture used is preferably a pure culture whereby the degree of purity must be sufficient to prevent substantial side effects. Preferably the pure culture is obtained from tobacco leaves. The microorganism culture can be preserved by freezing in liquid nitrogen and is thawed and reactivated before use. For immediate use, it can be kept in an active state in a biostat from which the continually required portions can be removed.

Characteristics of *Enterobacter aerogenes* are as follows:

| | |
|---|---|
| Motile rods | 0.3–1.5 μm |
| Gram | − |
| Development of gas at 37° C. | |
| Glycerin | + |
| Inositol | + |
| Andonitol | + |
| Voges-Proskauer | + |
| Methyl red | − |
| Phenylamine deaminase | − |
| Urease | −C |
| Catalase | + |
| Ornithine decarboxylase | + |
| Lysine decarboxylase | + |
| Hydrolyse of Aesculin | + |
| Growth: | |
| In presence of KCN | + |
| Upon Malonate as the only source of carbon | + |

The invention is exemplified by the descriptions hereinbelow.

EXAMPLE 1

Preparation of the Pure Culture

Twenty g of D-glucose, 8.6 g of peptone, 6.4 g of NaCl, 3.5 g of $KNO_3$; 4.5 g of $KH_2PO_4$, and 23.5 g of $Na_2HPO_4.2H_2O$ were dissolved in 1 liter of water. The thus obtained nutrient broth was divided into 5 equal aliquots of 200 ml each. Each aliquot was placed in a 500 ml Erlenmeyer flask, and the flasks were closed with a porous stopper in order to allow gases formed during the process to escape and to facilitate sterilization. The broths were sterilized and stored at 20° C.

One-hundred grams of dry Burley tobacco leaves were washed with 500 ml water under sterile conditions. One ml of the resulting wash suspension was drawn off under sterile conditions and added to aliquot I of the nutrient broth. Aliquot I was incubated on a shaker for 16 hours at 30° C. Then 1 ml of the incubated aliquot was removed under sterile conditions and inoculated into aliquot II of the nutrient solution, and the incubation was repeated. This serial transfer procedure was repeated until the fifth aliquot was treated.

After aliquot V had been incubated for 16 hours, it contained a pure culture of microorganisms of a genus Pseudomonas that derives its oxygen requirements via the reduction of nitrates and/or nitrites. The microorganisms of this pure culture were in their exponential growth phase and remained so for approximately 2 hours.

EXAMPLE 2

One kg of Maryland tobacco was processed to separate the stems from the strip. This yielded 250 g of stems and 750 g of strips. The 250 g of stems were washed with 1250 ml warm water at 70° C. This removed nitrates and nitrites contained in the stems together with other water-soluble components. The aqueous stem extract solution was separated from the stems, placed in a 2 liter Erlenmeyer flask, closed with a porous stopper, and cooled to 30° C. Then 12.5 g of D-glucose and 10 ml of the culture prepared in Example 1 was added to the flask. The microorganisms of the pure culture were still in their exponential growth phase.

The inoculated stem extract solution was incubated on a shaker at 30° C. for 16 hours at which time the anions of nitrate and/or nitrite were reduced to a content of 0.1 g per liter. The thus obtained denitrated stem extract solution was immediately centrifuged, and the residual microorganisms were removed.

The centrifuged, denitrated stem extract was reapplied to the predried, washed stems, which were then dried to a moisture level of 20%. In this manner, all of the soluble tobacco components that had been removed previously with the nitrates and/or nitrites were returned to the stems so that the stems contained essentially all of their original components with the exception of the nitrates and/or nitrites, which were reduced to 1/6 of their original content.

EXAMPLE 3

A tobacco stem extract was treated in a similar manner to Example 2. After separating the denitrated stem extract solution by centrifuging, the extract was applied to a different type of washed tobacco stems.

EXAMPLE 4

One kg of Maryland tobacco was destemmed and yielded 250 g of stems and 750 g of strips. The 250 g of stems were treated according to the process of Example 2. Following denitration, the active microorganisms, which were still in their exponential growth phase, were separated from the treated stems and yielded about 150 ml of material. The microorgansms were suspended and maintained in a nutrient broth comprising 30 g D-glucose, 12.9 g peptone, 9.6 g NaCl, 6.75 g $KH_2PO_4$, and 35.25 g $Na_2PO_4$ in 1500 ml of water.

The suspension of microorganisms was then sprayed evenly onto the 750 g of strips having a moisture content of 20%. After spraying, the strips had a moisture content of 50%. The tobacco was incubated at 30° C. for 24 hours under substantially anaerobic conditions. During this period, the nitrate and/or nitrite content of the tobacco was reduced to 1/20 of their original content. The denitrated strips were dried to a moisture content of 20%. This inactivated any microorganisms still remaining on the strips.

EXAMPLE 5

Two hundred fifty g of Burley tobacco leaves were washed in 1250 ml warm water at 70° C. The resulting tobacco extract solution was treated in a similar manner to Example 2. Thereafter, the denitrated tobacco extract solution was centrifuged to separate and recover the active microorganisms, and the denitrated extract was reapplied to the tobacco leaves.

EXAMPLE 6

One kg of tobacco scraps was ground to a granular size no greater than 150 μm. One hundred fifty ml of an active microorganism suspension obtained according to Example 1 and still in their exponential growth phase was maintained in their growth phase by adding the microorganisms to a broth containing 30 g D-glucose, 12.9 g peptone, 9.6 g NaCl, 6.75 g $KH_2PO_4$, and 35.25 g $Na_2PO_4.2H_2O$ in 1500 ml water. The suspension of active microorganisms was stirred into the powdered tobacco, and the resulting slurry was incubated for 24 hours at 30° C. in a 3 l Erlenmeyer flask equipped with a porous stopper. The microorganisms reduced the nitrates and/or nitrites contained in the tobacco slurry to 1/10 of the original content. Immediately afterwards, 150 g carboxymethylcellulose was stirred into the slurry, and the slurry was spread out in a layer of 3 mm thickness and dried to a 15% moisture content. This terminated the effect of the microorganisms and hardened the slurry into sheets of reconstituted tobacco, which were then ready for further processing.

EXAMPLE 7

In a similar manner to Example 2, a tobacco stem extract was inoculated with an inoculum as prepared in Example 1 and was then incubated on a shaker at 30° C. for 8 hours instead of 16 hours, so that the anions of nitrate and/or nitrite were reduced to a lesser extent than they were according to Example 2. The denitrated stem extract solution was further treated as in Example 2 and reapplied to the stems, predried, and washed as in Example 2. The stems were dried to a moisture content of 20%. The thus treated stems contained ⅓ of their original content of nitrate and/or nitrite.

EXAMPLE 8

In a similar manner to Example 4, tobacco strips were sprayed with a suspension of microorganisms to a moisture content of 50%. The mixture was incubated for 8 hours at 30° C. under substantially anaerobic conditions. During this time the microorganisms reduced the nitrate and/or nitrite contained in the strips to ¼ of their original content. The strips were then further treated as described in Example 4.

EXAMPLE 9

Tobacco stems were extracted according to the method of Example 2, and the extract was inoculated with a pure culture of bacteria *Enterobacter aerogenes* ATCC 13048. Incubation conditions and reapplication of the denitrated extract were identical to Example 2.

EXAMPLE 10

The process of Example 9 was repeated under identical conditions with the exception that the denitrated stem extract was reapplied to a different type of washed tobacco stems.

EXAMPLE 11

One kg Maryland tobacco was destemmed to yield 250 g stems and 750 g strips. The 250 g stems were treated as described in Examples 2 and 9. The strips were treated as described in Example 4 using the active microbial suspension obtained by treating the stems.

EXAMPLE 12

Two hundred fifty g of Burley tobacco leaves were washed in 1250 ml warm water at 70° C. The resulting tobacco extract solution was inoculated with *Enterobacter aerogenes* as in Example 8. Following denitration, the tobacco extract solution was centrifuged to separate the microorganisms. Thereafter, the extract was reapplied to the tobacco leaves.

EXAMPLE 13

Tobacco stems were prepared as in Example 9 and inoculated with a pure culture of *Enterobacter aerogenes*. The stem extract solution was incubated on a shaker at 30° C. for 8 hours so that the anions of nitrate and/or nitrite were reduced to a lesser extent than they were according to Example 7.

The denitrated stem extract solution was then treated as in Example 9 and reapplied to the stems, that has been predried and washed. The stems were dried to a moisture content of 20%. The thus treated stems contained ⅓ of their original content of nitrate and/or nitrite.

EXAMPLE 14

Maryland tobacco leaves were treated in a similar manner to Example 11 with the exception that they were incubated for 8 hours at 30° C. without air access. During this time the microorganisms reduced the nitrates and/or nitrites contanied in the strips to ¼ of their original content. The strips were then further treated as described in Example 11.

We claim:

1. A process for microbial reduction of the nitrate or nitrite content of tobacco comprising the steps of:

a. inoculating the tobacco with a pure culture of microorganisms selected from strains of *Enterobacter aerogenes* which derive their oxygen from the nitrates or nitrites in the tobacco and which are in their exponential growth phase;

b. incubating the inoculated tobacco with a nutrient solution under substantially anaerobic conditions for a period of time sufficient to degrade the nitrates or nitrites contained therein to a lower level; and c. thereafter terminating the activity of the microorganisms.

2. The process according to claim 1 wherein the tobacco is inoculated with a concentrated culture of *Enterobacter aerogenes* sufficient to degrade the nitrates or nitrites within an incubation period of about 12 to 24 hours and the effect of the microorganisms is terminated immediately after said period.

3. The process according to claim 1 wherein the pure culture of microorganisms is produced by inoculating a nutrient broth with an aqueous smear of nitrate-containing leaves or decayed leaves, said broth having a pH between about 6.6 and 7.5 and containing sufficient oxygen in the form of nitrates to support growth of the microorganisms; incubating said inoculated broth at a temperature between about 25° and 35° C. for about 15 to 25 hours with shaking under substantially anaerobic conditions; and thereafter serially inoculating fresh nutrient broth with the resulting culture and repeating the incubation until a pure culture is produced.

4. The process according to claim 1 wherein the microorganism is *Enterobacter aerogenes* ATCC 13048.

5. The process according to claim 1 wherein the tobacco to be treated comprises an aqueous tobacco stem extract containing soluble nitrates or nitrites.

6. The process according to claim 5 wherein the activity of the microorganisms is terminated by removing the microorganisms from the extract by filtration or centrifugation and thereafter the extract is reapplied to the extracted stems.

7. The process according to claim 1 wherein tobacco strips having a moisture content of about 10 to 30% are inoculated by spraying with an amount of a suspension of microorganisms in the nutrient solution which is sufficient to achieve a final moisture content of about 40 to 60%; the inoculated strips are incubated for about 12 to 24 hours; and the activity of said microorganisms is terminated after incubation by drying the denitrated strips to a moisture content of about 10 to 30%.

8. The process according to claim 7 wherein the suspension of microorganisms is obtained by inoculating a tobacco stem extract with a culture of microorganisms capable of degrading the nitrates or nitrites contained therein, incubating the inoculated extract under substantially anaerobic conditions until the microorganisms reach their exponential growth phase, thereafter isolating the microorganisms by centrifugation or filtration and suspending the isolated microorganisms in a nutrient solution.

9. The process according to claim 1 wherein the tobacco to be treated comprises a slurry of ground tobacco and water and the activity of the microorganisms is terminated by casting the slurry into or onto sheets and drying the sheets to a moisture content of about 10 to 30%.

* * * * *